United States Patent [19]

Danielsson et al.

[11] Patent Number: 4,938,226
[45] Date of Patent: Jul. 3, 1990

[54] METHOD AND AN APPARATUS FOR MEASURING BLOOD PRESSURE

[76] Inventors: Per Danielsson, Hantverkaregatan 13, S-341 00 Ljungby; Nels Henningsen, Sånekullavägen 35, S-217 74 Malmö ; Hans Coger, Torsgatan 105, S-341 00 Ljungby, all of Sweden

[21] Appl. No.: 303,670
[22] PCT Filed: Jul. 1, 1987
[86] PCT No.: PCT/SE87/00311
§ 371 Date: Jan. 17, 1989
§ 102(e) Date: Jan. 17, 1989
[87] PCT Pub. No.: WO88/00448
PCT Pub. Date: Jan. 28, 1988

[30] Foreign Application Priority Data
Jul. 15, 1986 [SE] Sweden .................... 8603115

[51] Int. Cl.⁵ .............................. A61B 5/022
[52] U.S. Cl. .................... 128/679; 128/686
[58] Field of Search .......... 128/672, 677–686, 128/327; 137/613; 251/120–122

[56] References Cited

U.S. PATENT DOCUMENTS

| 3,118,440 | 1/1964 | Dobbeleer | 128/679 |
| 3,741,199 | 6/1973 | Sharpe | 128/681 X |
| 3,954,099 | 5/1976 | Raczkowski et al. | 128/685 |
| 4,037,587 | 7/1977 | Kaneda et al. | 128/685 |
| 4,210,154 | 7/1980 | Klein | 128/686 X |
| 4,634,434 | 6/1987 | Marino, Jr. et al. | 604/249 X |

Primary Examiner—Angela D. Sykes
Attorney, Agent, or Firm—Ladas & Parry

[57] ABSTRACT

A method and apparatus for measuring blood pressure of persons of all ages. The apparatus comprises a cuff with two cushions which focus the pressure on an artery towards the skeleton. When pressing a first button, a valve system entails a slowly, controlled, continuous air outlet in order to make the reading of the systolic and diastolic pressure on a manometer possible.

7 Claims, 4 Drawing Sheets

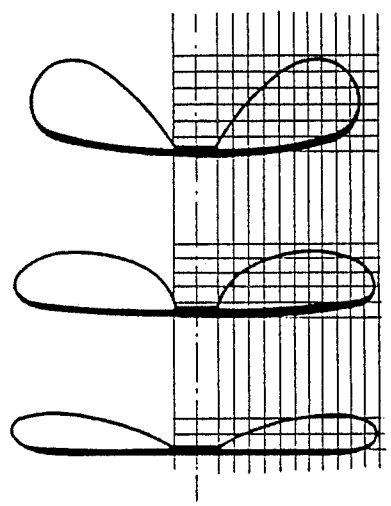
FIG. 3c
FIG. 3b
FIG. 3a
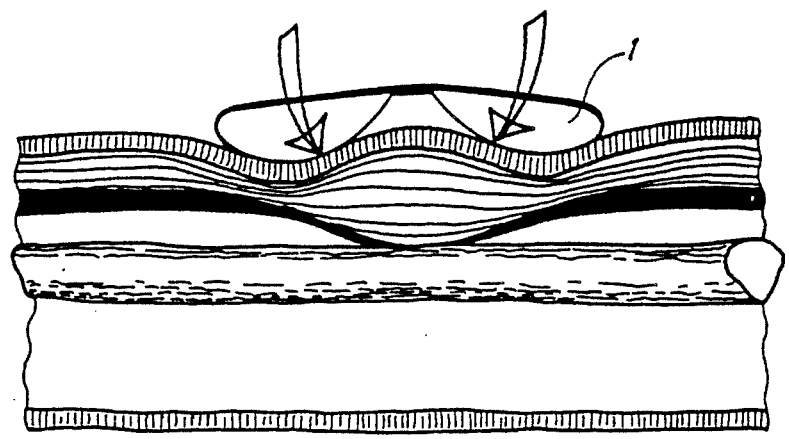
FIG. 4

METHOD AND AN APPARATUS FOR MEASURING BLOOD PRESSURE

FIELD OF THE INVENTION

The invention refers to a method for measuring blood pressure and an apparatus for carrying out the method. More in detail the invention refers to a method for measuring the blood pressure in such a way that the point of measuring is focused by means of a new cuff. Moreover, the apparatus according to the invention comprises a valve system which makes a carefully controlled air outflow possible.

PRIOR ART

A previously known apparatus for measuring the blood pressure with outside arranged accessories consists of a cuff which is connected to a manometer and an air hand pump with an air vent screw.

Today, measuring the blood pressure is the most common examination of all clinical tests performed by a physician. At least 10% of the adult population of Sweden is today treated for hypertonia, i.e. too high blood pressure. However, at least 25% of all persons are malpracticed due to an incorrect hypertonia diagnosis, especially due to erroneously performed blood pressure measuring. Furthermore, the cuff may cause such a pain that the blood pressure is raised during the measuring. A great amount of literature has been collected during the last 10 years.

The disadvantages with the present cuffs available on the market may be concluded according to the following:
1. the cuff squeezes the arm over a wide, vast area with the same width as the cuff, i.e. an extended "point of measuring",
2. many persons suffer due to that the cuff squeezes the arm in the present way,
3. the "object of measuring" may be thin, medium or coarse, which entails that several different sizes of cuffs are used,
4. when reading the systolic pressure it is not known at which point below the cuff the artery has allowed the blood stream to pass.

The difficulties in using said air vent screw on the air hand pump are:
1. that it may get stuck in opened and closed position, respectively,
2. that it does not give a continuous air outflow during the measuring due to the difficulty in finding the right position for the screw,
3. that it often gives employment injuries in the forefinger and thumb of the hospital staff, who are working continuously with measuring blood pressures at blood pressure centres and within medical attendance in general.

SUMMARY OF THE INVENTION

The invention comprises two devices, each separately constituting a new measuring instrument within the medical attendance for measuring blood pressure at hospitals, blood donation centres and elsewhere, where measuring blood pressure is involved in a routine for determining a person's blood pressure.

The first novelty is that the cuff consists of two parallel, inflatable intercommunicating rubber cushions. When air is inflated the cushions will grow in a radial and tangential direction towards each other. Thereby two fields of force are achieved, which are directed obliquely inwards against an extremity enclosed by the cuff and at the point where these cross each other an artery is positioned. This is squeezed towards the skeleton of the extremity so that the blood ceases to flow through and the so-called Korotkoff-sounds or the pulsation are not perceptible downstream the squeeze. The coarseness of the extremity is of less importance with this cuff, which eliminates one problem for the hospital staff.

The second novelty is the embodiment of the valve system.

The cuff is connected to a valve system with a rubber hose. An air hand pump is also connected to the valve system, i.e. through the valve system a tube is running, which partly transports the air from the air pump to the cuff, partly discharges the air from the cuff via two small channels placed across the tube.

Said two small channels are of different sizes and each of them is closed by means of a rubber coated piston, each one giving the air required outflow. Each of the pistons are operated by means of a button. There is a smaller channel for slow, continuous emptying, and a bigger channel for rapid emptying, when the measuring is accomplished.

When the rubber cushions are inflated to a pressure which prevents the blood to pass the Korotkoff-sounds are inaudible downstreams the squeeze. Air is now released by a press on the first button, which lifts the rubber coated piston and the smaller channel opens and a distinct, continuous air outflow starts. After a certain period of time, as the pressure sinks, the Korotkoff-sounds begin to be heard, i.e. the heart now succeeds in pressing blood past the squeeze and the systolic pressure is read. The air outflow may be stopped by releasing the first button. However, a person skilled at measuring blood pressure lets the air continue to flow out and lets the pressure fall continue until the Korotkoff-sounds once more completely cease, whereby the diastolic pressure is read, which means the lowest pressure of the blood during the expansion moment of the heart. In order that the cuff will let go the hold of the arm the second button is now pressed down, which opens a coarser channel in a similar way, as does the first button. Thanks to this button system instead of a screw, the staff does not need to search for the right emptying position of the screw, whereby injuries on forefinger and thumb are avoided.

From the above-mentioned it is evident that staff having measuring of blood pressure as a routine in their daily work obtains an instrument which is considerably easier to handle and safer for the reasons that:
a. the cuff suits everybody, i.e. no difficulties in finding a suitable cuff,
b. the patient feels less pain by the pressure from the cuff,
c. the staff is spared from several inflations due to missing the right air outflow when screwing the air vent screw,
d. the screwing is not needed any longer, which entails no more employment injuries on forefinger and thumb,
e. the reading of the manometer is safer followed by better diagnosis and safer medication,
f. the cuff has a smaller pressure area than the conventional cuff.

The new cuff with double cushions is a great improvement of the blood pressure cuff and will not only facilitate the work of the hospital staff but also entail that patients of all ages and sexes achieve a measuring of blood pressure with less pain and are also spared other painful incisions and dosages of medications which in turn may entail too soon a decease. The cuff has been developed in theory and practice as well as the pertaining valve system, which as a blood pressure measuring unit more than well fulfill the desiderata mentioned under the heading Prior art.

BRIEF DESCRIPTION OF THE DRAWINGS

The invention is described more in detail below by means of a non-limiting preferred embodiment with reference to the enclosed drawings.

FIGS. 3a, 3b and 3c show the cross-section of the rubber cushions at different pressures during the inflation. FIG. 4 shows the rubber cushions at loading with the pertaining field of power schematically drawn.

DETAILED SPECIFICATION OF PREFERRED EMBODIMENTS

Figure 1:
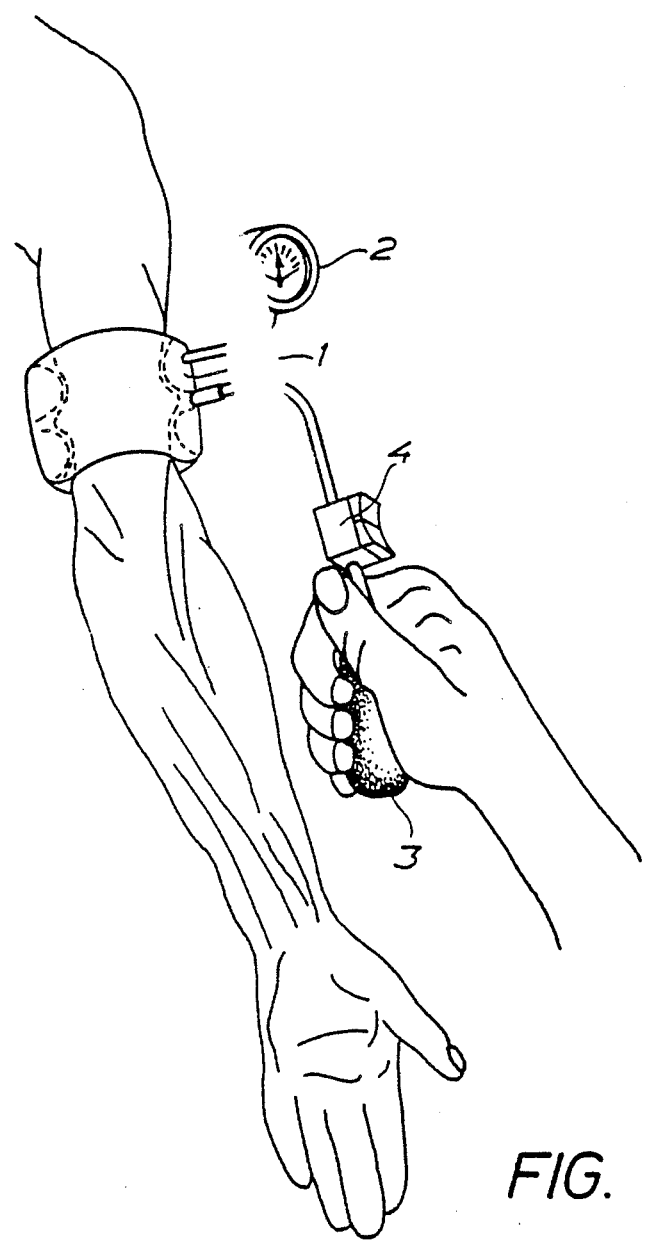
FIG. 1 is a perspective view and shows a cuff mounted on an over-arm with a coupled manometer, whereby an air hand pump is connected to a valve system.

FIG. 1 shows the measuring apparatus according to the invention attached to an over-arm The apparatus for measuring the blood pressure consists of a cuff 1, a manometer 2, an air hand pump 3 and a valve system 4.

Figure 3:
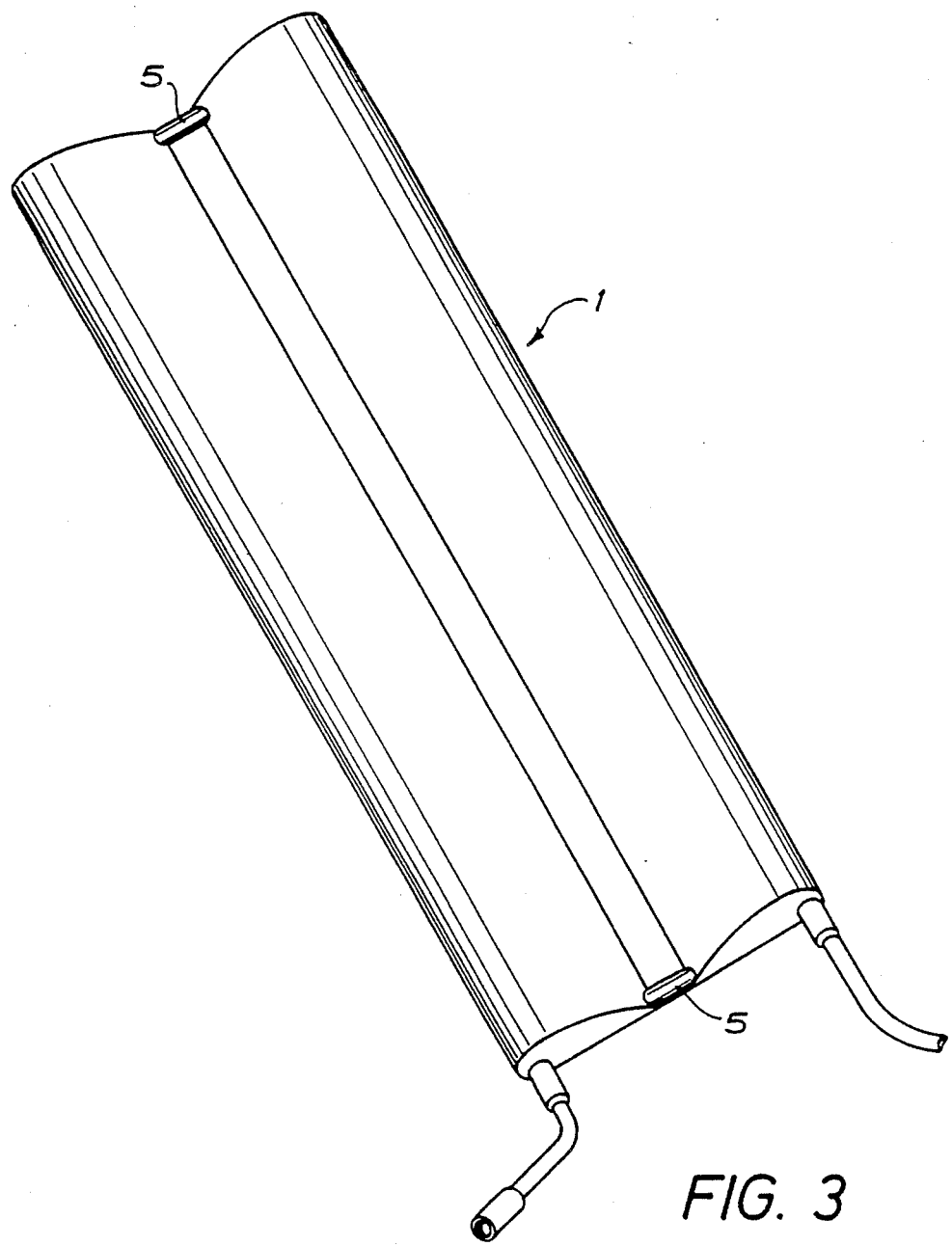
FIG. 3 is a perspective view of the cuff, whereby the cross-sectional

The cuff 1 is provided with two rubber cushions, which are positioned in parallel and are interconnected by means of two channels 5, one at each short end of the cuff as shown in FIG. 3.

The cross-section of the cuff during the inflation at different air pressures is presented in FIGS. 3a, 3b and 3c. From this the shape and characteristics of the cushions appear during the inflation. The envelope surfaces of the cushions do not move only radially but also tangentially which entails that skin, underlying tissues and blood vessels, in this case the artery of the over-arm, are pressed towards a certain point, where the fields of force of the rubber cushions cross each other and with a mutual force presses the vein towards the skeleton so that the Korotkoff-sounds cease and the blood stops, cf. FIG. 4. Thereby the Korotkoff-sounds cease in a stethoscope which is placed towards the artery in the bend of the arm downstream the cuff.

The manometer 2 for reading the pressure may be a mercury column or an aneroid, connected by means of a hose to the cuff or may in any other way be an apparatus connected for electrical or digital reading.

Figure 2:
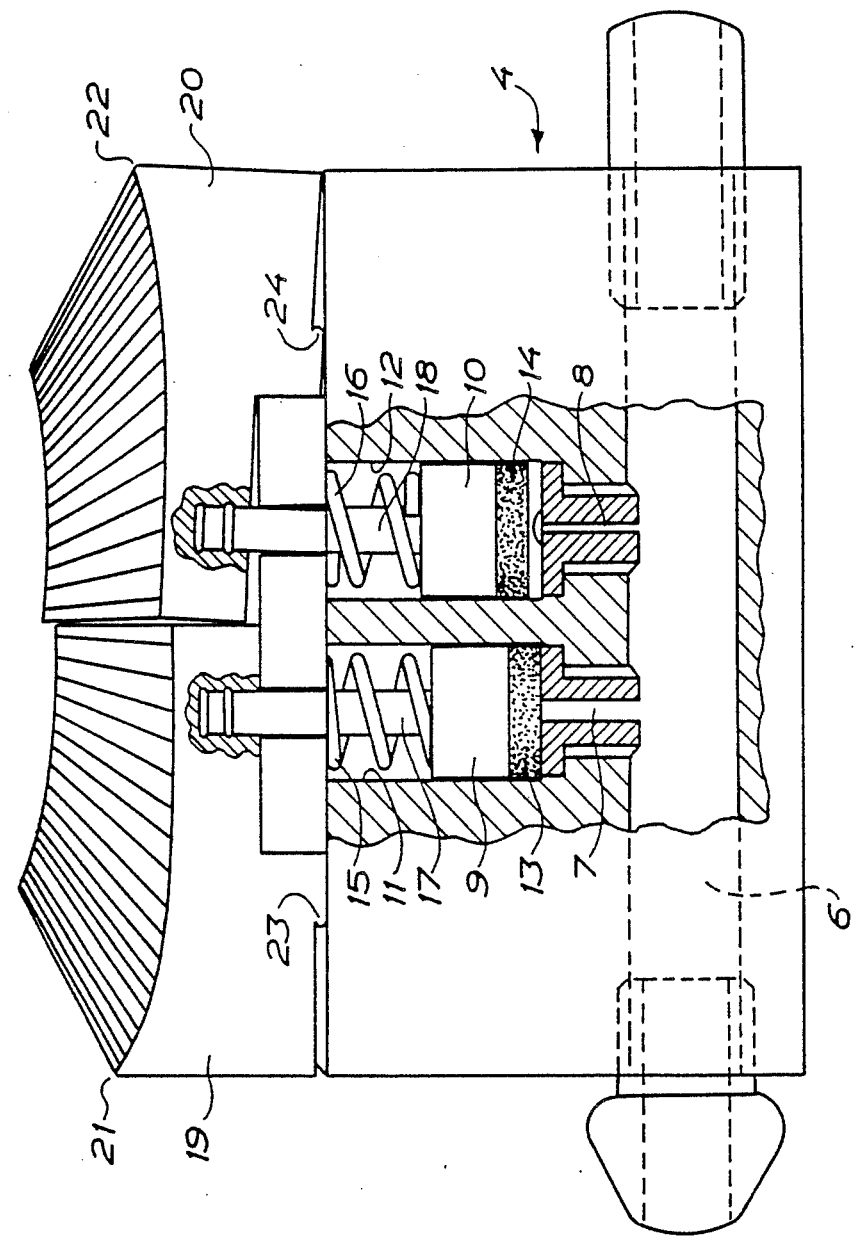
FIG. 2 is a perspective view partly in cross-section of the valve system.

An air hand pump 3 provides the cushions with air by means of several presses by one hand to the moment when the Korotkoff-sounds cease, as previously known The valve system is at one end side connected to the air hand pump 3 and at its other end side connected to the cuff 1. In the valve system 4 two channels 7, 8 are perpendicularly connected to a tube 6 extending between the air hand pump 3 and the cuff 1 as appears from FIG. 2. Each channel 7, 8 ends with a valve seat coopering with a piston 9, 10, which runs in a cylinder barrel 11, 12 in the valve system 4. At the end facing the channel 7, 8 each piston 9, 10 is rubber coated as at 13, 14. When operating the piston the channels 7, 8 open and close. The pistons 9, 10 are loaded by means of springs 15, 16 towards the position where the channels 7, 8 are closed. The pistons 9, 10 are attached to piston rods 17, 18 which in turn are releasably attached to buttons 19, 20. The top surface of the button is rifled in order to offer a safe operation surface. When pushing down the outer edge 21, 22 of the button, the button will pivot around a lever point 23, 24 in order to lift the piston rod and the piston thereby opening the corresponding channels 7, 8 so that the tube 6 is opened to the atmosphere via one of the channels 7, 8.

A light pressure on the button, closest to the hand 20 (see FIG. 1), opens the smaller channel 8, the diameter of which is some tenths of a mm. The small area of the channel makes the air outflow from the tube 6 to the atmosphere via the channel 8 to be discharged so slowly that the person who reads the pressure has time to read the systolic pressure on the manometer 2 when the Korotkoff-sounds return. The air outflow slowly continues until the Korotkoff-sounds cease, when the artery no more is prevented by any pressure from the outside, i.e. the blood flows freely in the vein and the diastolic pressure is read. Then the second button is pressed down, and the largest air channel 7 is opened by means of lifting the spring-loaded and rubber coated piston 13 from the valve seat.

In each piston 9, 10 longitudinal grooves (not shown) are to be found which facilitate the passage of the air out into the open atmosphere.

With the cuff according to the present invention the thickness of the arm is of less importance. Either the arm is thin or thick the parallel rubber cushions will press the artery towards the skeleton and stop the blood flow The construction of the valve seat with raising pistons is one of several solutions, for which reason the construction shown has been chosen for its simplicity with regard to use and construction.

In order to obtain the correct air outflow through the thin channel 8 tests have been made on laboratory basis. Modifications may be required after a certain time of tests at hospitals and other institutions. The connections for the cuff 1 and the air hand pump 3, respectively, are of standard type and may be threaded into the valve system 4 or as an alternative casted at the manufacture.

The intention with this new cuff is to focus the field of force of the rubber cushions against an area, where an artery may be pressed towards a skeleton, cf. FIG. 4. The force required to stop the blood flow in the artery is F Newton per unity of length extremity. The force F is distributed over two rubber cushions and from this F/2 is given from each cushion perpendicular towards the artery. The resultant force exerted by the cuff, if the cushion forms an angle $\alpha$ with a line perpendicular to the artery, is equal to $$\frac{F}{2 \cos \alpha}$$

i.e. the resultant is greater than F/2. Suppose that $\alpha$ (alfa) is equal to 45°, then the resultant is approximately similar to 0,7 F, giving a smaller force against the nerve-circuits under the leather-skin. In order to obtain a field of force, where the length of the force arrows represents where the greatest expansion $\delta$ is to take place and under which angle α, we principally regard an expression according to the mechanics of materials $$\frac{F}{A} = P = \frac{\sigma_{MAT} \times 2t}{D}$$

$$\delta = \frac{P \times D^2}{E \times 2t}$$

where
- A is the area within which F presses on the extremity
- P is the prevailing pressure in the cushions
- σMat is the resistance to rupture for the cushion t is the thickness of goods
- D is the diameter of the cushion parallel to the artery
- E is the elasticity module for the material in the cushion δ is the expansion of the cushion The only unknown variable in the expression for the expansion δ above is the thickness of goods t. If we allow t to increase, δ decreases, i.e. a low stretching is achieved, and if we decrease t, δ increases, i.e. a higher stretching is achieved. From this reasoning we choose t so that each cushion expands according to the curvature defined in FIG. 3c. The thickness of material of the cushion becomes the largest on the outside and towards the edge and decreases on the inside towards the centre line within a sector of between 20°–50°.

Contrary to the conventional cushions our rubber cushions exert about 30% lower pressure on the nerve-circuits under the leather-skin thanks to the position and construction of the double rubber cushions, which entail less pain for the patient. Moreover, the determination of the exact measuring values of the blood pressure is improved, since the width of the measuring area is decreased 10 times from about 10–12 cm to 1,0–1,5 cm.

We claim:

1. An apparatus for measuring blood pressure by means of a blood pressure cuff comprising two parallel, physically interconnected and pneumatically communicating cushions having an outer surface, which, at inflation, achieves a substantially continuously vaguely rounded shape, and an inner surface, for contact with an extremity, the blood pressure of which is to be monitored, having two separate areas of contact with said extremity.

2. The apparatus as claimed in claim 1, wherein said two separate areas of contact with said extremity form, at inflation, two fields of forces directed obliquely towards each other and towards said extremity in order to stop the blood flow in an artery positioned therebelow by squeezing the artery towards an underlying skeleton within an area focused by the two cushions.

3. The apparatus as claimed in claim 1, wherein the cushions are asymmetrically shaped so that the cushions are expanded in relation to the distance from a centre line of the cuff, whereby the inner surface of the cuff facing the extremity is substantially double drop-shaped with the tips thereof facing towards the centre line of the cuff.

4. The apparatus as claimed in claim 3, wherein the asymmetrical shape is obtained by a variable material thickness in the cushions.

5. The apparatus as claimed in claim 4, wherein the material in the outer surface of the cuff is considerably thicker than the material in the inner surface of the cuff facing the extremity.

6. A method of measuring blood pressure by means of a blood pressure cuff comprising the steps of:
   positioning the cuff, having two parallel, physically interconnected and pneumatically communicating cushions, on an extremity, the blood pressure for which is to be monitored;
   inflating said cushions by an air hand pump to form two fields of forces directed obliquely towards each other and towards the extremity in order to stop the blood flow in an artery positioned therebelow by squeezing the artery towards an underlying skeleton within an area focused by the two cushions; and
   reading the blood pressure by a pressure meter.

7. The method as claimed in claim 6, comprising the step of further inflating the cushions whereby each cushion achieves a shape wherein each cushion is progressively further expanded in relation to the distance from a centre line of the cuff, whereby the inner surface of the cuff facing the extremity becomes substantially double drop-shaped with the tips thereof facing towards the centre line of the cuff.

* * * * *